United States Patent
Kitano et al.

(10) Patent No.: US 10,499,648 B2
(45) Date of Patent: Dec. 10, 2019

(54) STERILIZATION METHOD, FORMULATION FOR STERILIZATION USE, AND DEVICE FOR PRODUCING STERILIZING LIQUID

(71) Applicants: Katsuhisa Kitano, Ibaraki (JP); Atsushi Tani, Toyonaka (JP); Satoshi Ikawa, Sakai (JP); Yoichi Nakashima, Ibaraki (JP)

(72) Inventors: Katsuhisa Kitano, Ibaraki (JP); Atsushi Tani, Toyonaka (JP); Satoshi Ikawa, Sakai (JP); Yoichi Nakashima, Ibaraki (JP)

( * ) Notice: Subject to any disclaimer, the term of this patent is extended or adjusted under 35 U.S.C. 154(b) by 0 days.

(21) Appl. No.: 15/446,155

(22) Filed: Mar. 1, 2017

(65) Prior Publication Data

US 2017/0172149 A1 Jun. 22, 2017

Related U.S. Application Data

(63) Continuation-in-part of application No. PCT/JP2015/004470, filed on Sep. 2, 2015.

(30) Foreign Application Priority Data

Sep. 2, 2014 (JP) .............................. 2014-0178467

(51) Int. Cl.
*A01N 59/00* (2006.01)
*A61L 2/18* (2006.01)

(52) U.S. Cl.
CPC ................ *A01N 59/00* (2013.01); *A61L 2/18* (2013.01); *A61L 2202/11* (2013.01)

(58) Field of Classification Search
None
See application file for complete search history.

(56) References Cited

U.S. PATENT DOCUMENTS

| 3,364,037 A | 1/1968 | Mink |
| 3,593,928 A * | 7/1971 | Friedland .............. B01F 3/1271 241/14 |
| 2010/0019677 A1 | 1/2010 | Kitano et al. |
| 2010/0209293 A1 | 8/2010 | Ikawa et al. |
| 2012/0156093 A1 | 6/2012 | Kitano |
| 2015/0010430 A1 | 1/2015 | Kitano et al. |
| 2015/0086423 A1 | 3/2015 | Kitano et al. |

FOREIGN PATENT DOCUMENTS

| CN | 102625730 A | 8/2012 |
| EP | 2 206 521 A1 | 7/2010 |
| EP | 2206521 * | 7/2010 |
| EP | 2 474 352 A1 | 7/2012 |
| EP | 2 804 448 A1 | 11/2014 |
| JP | H07-25178 A | 1/1995 |
| JP | 2002-265387 A | 9/2002 |
| JP | 2002-326922 A | 11/2002 |
| JP | 2005-170849 A | 6/2005 |
| JP | 4408957 B | 2/2010 |
| JP | 5305274 B | 10/2013 |
| WO | 2006/079109 A2 | 7/2006 |
| WO | 2008/072390 A1 | 6/2008 |
| WO | 2009/041049 A1 | 4/2009 |
| WO | 2011/027542 A1 | 3/2011 |
| WO | 2013/105659 A1 | 7/2013 |
| WO | 2013/161327 A1 | 10/2013 |

OTHER PUBLICATIONS

Appelman et al. (Aqueous Peroxynitric Acid (NOONO2): A Novel Synthesis and Some Chemical and Spectroscopic Properties. 1994.*
Appelman et al. Aqueous Peroxynitric Acid (NOONO2): A Novel Synthsis and Some Chemical and Spectrocopic Properties. 1994.*
Heaselgrave et al. "Acidified nitrite enhances hydrogen peroxide disinfection of Acanthamoeba, bacteria and fungi". 2010.*
Naitali et al. "Combined Effects of Long-Living Chemical Species during Microbial Inactivation Using Atmospheric Plasma-Treated Water". 2010.*
Kagakudaijiten Henshuiinkai Kagakudaijiten 8 Syukusatuban DAI16SATU Kyoritsu Shuppan Co., Ltd. Mar. 10, 1974, p. 408 (translation: ed. by Encyclopedia Chimica 8, Board of Editors, Encyclopedia Chimica 8, miniature version, 16th printing) and a partial translation. (3 pages).
Kitano et al., "Cryopreservation of plasma treated water (PTW) for disinfection," 5th International Conference on Plasma Medicine (ICPM5), May 2014, http://icpm5.plasmabio.com. (1 page). Kitano et al., "Sequential production of high concentration plasma treated water for disinfection," The Japan Society of Applied Physics, Spring Lecture Presentation, Mar. 2014, https://confit.atlas.jp/guide/event/jsap2014s/top. (2 pages).
Kitano et al., "Strong bactericidal activity of the plasma treated water for medical application based on the reduced pH method," 8th International Conference on Reactive Plasmas/31st Symposium on Plasma Processing, Feb. 2014, http://plasma.ed.kyushu-u.ac.jp/~icrp-8/. (2 pages).
Zhu et al., "Bactericidal Activity of Peroxynitrite," Archives of Biochemistry and Biophysics,vol. 298, No. 2, Nov. 1, 1992, pp. 452-457. (6 pages).
International Preliminary Report on Patentability dated Jul. 14, 2016 in corresponding PCT Patent Application No. PCT/JP2015/004470 and a partial translation. (7 pages).

(Continued)

*Primary Examiner* — Robert A Wax
*Assistant Examiner* — Danah Al-Awadi
(74) *Attorney, Agent, or Firm* — Buchanan Ingersoll & Rooney PC

(57) ABSTRACT

A sterilization method is provided which acquires microbicidal activity equivalent to plasma-treated solution or more powerful than the same without the use of a plasma generation device. The sterilization method includes applying liquid containing peroxynitric acid ($HOONO_2$) produced by chemical reaction to an object to be sterilized under acidic conditions of a pH value of 4.8 or lower. The liquid containing the peroxynitric acid is produced by mixing nitrous acid and peroxide together, for example, mixing nitrite and peroxide together.

8 Claims, 14 Drawing Sheets

(56) References Cited

OTHER PUBLICATIONS

Written Opinion of the International Preliminary Examining Authority dated May 10, 2016 in corresponding PCT Patent Application No. PCT/JP2015/004470 and a partial translation. (7 pages).
International Search Report dated Oct. 13, 2015 in corresponding PCT Patent Application No. PCT/JP2015/004470 and a partial translation. (5 pages).
Written Opinion of the International Searching Authority dated Oct. 13, 2015 in corresponding PCT Patent Application No. PCT/JP2015/004470 and a partial translation. (6 pages).
Written Reply to the International Search Report and a partial translation, for PCT/JP2015/004470, dated Oct. 13, 2015 (12 pages).
Partial Supplementary European Search Report dated Apr. 9, 2018, by the European Patent Office in corresponding European Patent Application No. 15837245.8 (14 pages).
The Extended European Search Report dated Aug. 16, 2018, by the European Patent Office in corresponding European Patent Application No. 15837245.8. (17 pages).
Robinson et al., "Synthesis of Peroxynitrite from Nitrite and Hydrogen Peroxide," Methods in Enzymology, (2005), vol. 396, pp. 207-214.
Saha et al., "Determination of Optimal Conditions for Synthesis of Peroxynitrite by Mixing Acidified Hydrogen Peroxide with Nitrite," Free Radical Biology & Medicine, (1998), vol. 24, No. 4, pp. 653-659.
The Extended European Search Report dated May 22, 2019, by the European Patent Office in corresponding European Patent Application No. 15837245.8. (8 pages).

\* cited by examiner

MAGNETIC FIELD(mT)

STERILIZATION METHOD, FORMULATION FOR STERILIZATION USE, AND DEVICE FOR PRODUCING STERILIZING LIQUID

CROSS-REFERENCE TO RELATED APPLICATIONS

This application is a continuing application, filed under 35 U.S.C. § 111(a), of International Application PCT/JP2015/004470, filed on Sep. 2, 2015, the entire contents of which are incorporated herein by reference.

FIELD

The present invention relates to a sterilization method, formulation for sterilization use, and a device for producing sterilizing liquid. The sterilization method and the formulation for sterilization use according to the present invention are used for: sterilization or complete sterilization of medical equipment, food containers, foods, and other articles; sterilization or complete sterilization for odontotherapy; sterilization, complete sterilization, or disinfection of pathogenic microorganisms in stomach, and of wound area (wounds); sewage treatment; and sterilization of other various targets.

BACKGROUND

Conventionally, methods for sterilizing or completely sterilizing various microorganisms such as bacteria or viruses can be broadly divided into two types, i.e., a physical method (mechanical method) using heat, pressure, or the like, and a chemical method using chemical agents.

According to the physical method, the type of an object to be sterilized is limited because the object to be sterilized is exposed to extreme physical conditions in many cases. In the case of the chemical method, chemical agents to be used may exert a harmful influence on the human body. Therefore, the chemical method involves a process for securely rendering the residual agent harmless, which consequently requires more cost and time.

The inventors of the present invention previously proposed the sterilization method using low-temperature plasma generated under an atmospheric pressure (WO2009/041049; "Strong bactericidal activity of the plasma treated water for medical application based on the reduced pH method" by Katsuhisa Kitano, Satoshi Ikawa, Atsushi Tani, Yoichi Nakashima, and Tomoko Ohshima on February 2014, 8th International Conference on Reactive Plasmas/31st Symposium on Plasma Processing, http://plasma.ed.kyushu-u.ac.jp/icrp-8/; "Sequential production of high concentration plasma treated water for disinfection" by Katsuhisa Kitano, Satoshi Ikawa, Yoichi Nakashima, and Atsushi Tani, on March 2014, The Japan Society of Applied Physics, Spring Lecture Presentation, https://confit.atlas.jp/guide/event/jsap2014s/top"; and "Cryopreservation of plasma treated water (PTW) for disinfection" by Katsuhisa Kitano, Satoshi Ikawa, Yoichi Nakashima, and Atsushi Tani on May 2014, 5th International Conference on Plasma Medicine (ICPM5), http://icpm5.plasmabio.com/). The sterilization method is a method for sterilizing microorganisms present in a liquid or on a surface thereof by generating plasma in a vicinity of or in a manner to make contact with a liquid whose pH value is adjusted to become 4.8 or lower and allowing radicals generated by the plasma to make contact with the liquid. According to the sterilization method, superoxide anion radicals ($O_2^-$.) that are generated by the plasma are diffused into the liquid, and the diffused superoxide anion radicals ($O_2^-$.) react with protons ($H^+$) in the liquid to thereby form hydroperoxy radicals (HOO.). The concentration of hydroperoxy radicals (HOO.) is increased by adjusting a pH value of the liquid to become 4.8 or lower, so that powerful microbiocidal activity is attained.

Another sterilization method has been proposed in which plasma is generated in a manner not to contact a liquid, active species generated by the plasma are electrophoresed to contact with the liquid, and thereby, the liquid is sterilized (WO2011/027542).

The plasma generation device used for the sterilization methods is disclosed in WO2008/072390.

However, in order to use plasma for odontotherapy or for sterilization and disinfection of medical equipment, for example, a plasma generation device should be installed in a place where medical treatment is provided, and further, a pipe line for introducing different types of gases should be provided. This causes problems related to cost and space.

In order to solve the problems, the inventors of the present invention proposed a sterilization method. The method includes using plasma to produce a plasma-treated solution in which biocidal activity is held; freezing the plasma-treated solution to produce solid ice and store the solid ice in a frozen state; carrying the solid ice to a place where medical treatment is provided; thawing, in the place, the solid ice to return to the plasma-treated solution in which biocidal activity is held; and using the plasma-treated solution to apply a sterilization treatment (WO2013/161327).

As discussed above, the use of plasma or the use of a plasma-treated solution produced by physical reaction by the plasma achieves powerful microbicidal activity. It is known that the microbicidal activity of the plasma-treated solution comes from the hydroperoxy radicals (HOO.). However, it was not revealed what supplies the hydroperoxy radicals (HOO.). In other words, it was previously unknown what kind of substance is a precursor of the hydroperoxy radicals (HOO.).

If the precursor of the hydroperoxy radicals (HOO.) were identified, and further, if the substance identified were synthesized by chemical reaction, hydroperoxy radicals (HOO.) having higher concentration could be supplied, leading to the possibility of achieving more powerful microbicidal activity.

The inventors of the present invention have continued to conduct further researches and experiments. The inventors then successfully identified what kind of substance supplies the hydroperoxy radicals (HOO.) to produce powerful microbicidal activity. Further, the inventors obtained knowledge about a method for efficiently synthesizing the substance by chemical reaction, and about conditions necessary to perform powerful sterilization using the synthesized substance.

SUMMARY

The present invention has been achieved based on the new discovery and knowledge, and an object thereof is to provide a sterilization method for acquiring microbicidal activity equivalent to the plasma-treated solution or more powerful than the same without the use of a plasma generation device, formulation for sterilization use, and a device for producing sterilizing liquid.

A sterilization method according to one embodiment of the present invention includes applying liquid containing peroxynitric acid ($HOONO_2$) produced by chemical reaction to an object to be sterilized under acidic conditions of a pH value of 4.8 or lower.

A formulation for sterilization use according to one embodiment of the present invention is a formulation for sterilization use applied to an object to be sterilized to sterilize the object. The formulation for sterilization use includes a first case containing nitrite or a precursor of the nitrite; a second case containing peroxide or a precursor of the peroxide; and a third case configured to obtain liquid containing peroxynitric acid by mixing together the nitrite or the precursor of the nitrite taken from the first case and the peroxide or the precursor of the peroxide taken from the second case.

According to the present invention, without the use of a plasma generation device and so on, microbicidal activity equivalent to the plasma-treated solution or more powerful than the same can be obtained.

DESCRIPTION OF EMBODIMENTS

Outline of Embodiments of the Invention

Figure 1:
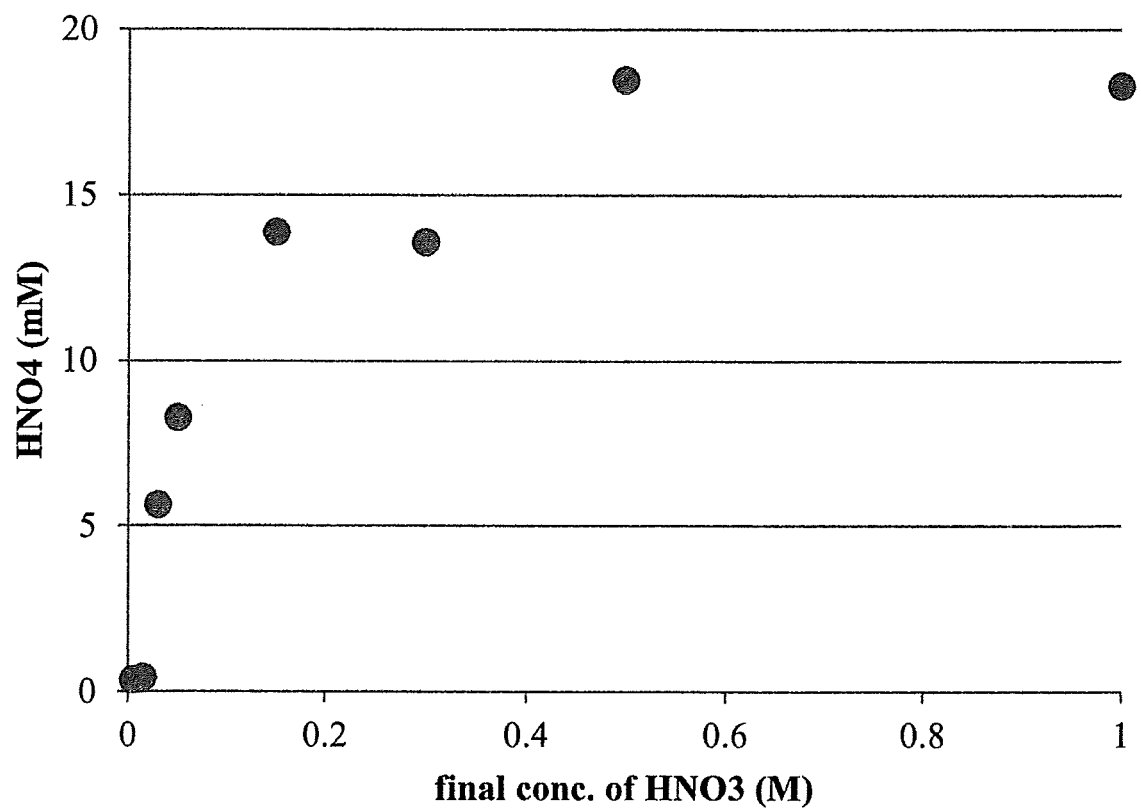
FIG. 1 is a diagram showing a relationship between the concentration of peroxynitric acid produced in a first embodiment and the concentration of nitric acid.

The present invention may be implemented in various embodiments described below.

To be specific, a sterilization method according to an embodiment includes applying liquid containing peroxynitric acid ($HOONO_2$) produced by chemical reaction to an object to be sterilized under acidic conditions of a pH value of 4.8 or lower.

At this time, the liquid containing the peroxynitric acid is produced by mixing nitrous acid and peroxide together, for example, by mixing nitrite and peroxide together. The nitrous acid or the nitrite may be substance, gas, or the like which can produce the nitrous acid or the nitrite.

Acid is mixed with liquid in which nitrite and peroxide are mixed to produce liquid having a pH value of 4.8 or lower, and the liquid having a pH value of 4.8 or lower is applied to the object to be sterilized, for example.

Alternatively, the peroxynitric acid is synthesized, by mixing nitrite, peroxide, and acid together to produce liquid having a pH value of 2 or lower, then to produce liquid containing the peroxynitric acid, buffer solution is used to dilute the liquid containing the peroxynitric acid to produce liquid having a pH value of 3 to 4.8, and the liquid having a pH value of 3 to 4.8 is applied to the object to be sterilized.

The acid is mixed with the peroxide to produce liquid having a pH value of 2 or lower, and the liquid having a pH value of 2 or lower is mixed with the nitrite to synthesize the peroxynitric acid, for example.

The liquid is adjusted to have a temperature of 10° C. or lower when the peroxynitric acid is synthesized, thereafter, the temperature of the liquid is increased, and the liquid is adjusted to have a temperature of 20° C. or higher when the liquid is applied to the object to be sterilized, for example.

The nitrite is sodium nitrite ($NaNO_2$) and the peroxide is hydrogen peroxide ($H_2O_2$), for example.

The acid is nitric acid ($HNO_3$), for example.

A formulation for sterilization use according to one embodiment is a formulation for sterilization use applied to an object to be sterilized to sterilize the object. The formulation for sterilization use includes a first case containing nitrite or a precursor of the nitrite; a second case containing peroxide or a precursor of the peroxide; and a third case configured to obtain liquid containing peroxynitric acid by mixing together the nitrite or the precursor of the nitrite taken from the first case and the peroxide or the precursor of the peroxide taken from the second case.

Preferably, the formulation for sterilization use includes acid for adjusting the liquid mixed in the third case to become a pH value of 2 or lower, and further includes buffer solution to dilute liquid produced after the mixture in the third case to become a pH value of 3 to 4.8 in order to apply the liquid to the object to be sterilized.

A production device for producing sterilizing liquid according to one embodiment includes a first tank configured to contain nitrite therein; a second tank configured to contain peroxide therein; a third tank configured to mix together the nitrite sent out from the first tank and the peroxide sent out from the second tank to produce liquid containing peroxynitric acid; an acid pipe line configured to supply acid for adjusting the liquid mixed in the third tank to become a pH value of 2 or lower; a cooling device configured to cool the liquid in the third tank; and a retrieval line configured to take the liquid containing the peroxynitric acid from the third tank.

A treatment by sterilizing liquid according to one embodiment is performed by applying liquid containing peroxynitric acid ($HOONO_2$) obtained by chemical reaction to a living body under acidic conditions of a pH value of 4.8 or lower to sterilize the living body.

It is noted that, in the Specification, lowering concentration of the number of living microorganisms is referred to as "sterilization".

Producing Peroxynitric Acid by Chemical Reaction

The description goes on to a method for producing (synthesizing) peroxynitric acid (pernitric acid) by chemical reaction.

To be specific, peroxide reacts with nitrous acid to produce peroxynitrite (peroxynitrous acid), and then, the peroxynitrite reacts with peroxide to produce peroxynitric acid. In such a case, the chemical reaction (synthesis reaction) with hydrogen peroxide used as the peroxide is represented by Formulas (1), (2), and (3) as follows.

$$HNO_2 + H_2O_2 \rightarrow HOONO + H_2O \tag{1}$$

$$HOONO + H^+ \rightarrow NO_2^+ + H_2O \tag{2}$$

$$NO_2^+ + H_2O_2 \rightarrow HOONO_2 + H^+ \tag{3}$$

To be more specific, as shown in Formula (1), hydrogen peroxide ($H_2O_2$) reacts with nitrous acid ($HNO_2$) to produce peroxynitrite (HOONO). The peroxynitrite has a short lifetime. As shown in Formula (2), the peroxynitrite reacts with protons (H+) under acidic conditions to thereby produce nitronium ions ($NO_2^+$) and water ($H_2O$). The nitronium ions ($NO_2^+$) have an extremely short lifetime and are unstable. The nitronium ions ($NO_2^+$) therefore react with the hydrogen peroxide promptly to produce peroxynitric acid ($HOONO_2$) and protons. Since the nitronium ions ($NO_2^+$) have an extremely short lifetime, it can be said that the peroxynitrite reacts with the hydrogen peroxide to produce the peroxynitric acid. The foregoing reaction progresses under strongly acidic conditions.

The peroxynitrite is an intermediate which is produced as shown in Formula (1) and is decomposed as shown in Formula (2). In the process of reaction, hydrogen peroxide is used twice. It is thus necessary to prepare hydrogen peroxide two times more than nitrite.

The decomposition reaction of peroxynitric acid is represented by Formulas (4) and (5) as follows.

$$HOONO_2 \rightarrow HNO_2 + O_2 \tag{4}$$

$$HOONO_2 + HNO_2 \rightarrow 2HNO_3 \tag{5}$$

To be more specific, peroxynitric acid autolyzes to produce nitrous acid as shown in Formula (4). Further, as shown in Formula (5), the peroxynitric acid reacts with the nitrous acid which has been produced by the autolysis of the peroxynitric acid, to thereby be decomposed so that nitric acid ($HNO_3$) is then produced. In this way, all of the peroxynitric acid is eventually decomposed into nitric acid and oxygen.

Meanwhile, in Formula (1), the nitrous acid ($HNO_2$) itself is unstable. Even if being produced, the nitrous acid disappears in a few minutes to a few hours. It is therefore not available in market. For this reason, in order to chemically synthesize peroxynitric acid ($HOONO_2$), solution of nitrite is used and the solution is adjusted to become acidic, so that nitrous acid is temporally produced in the solution. In short, nitrite and acid are used in order to synthesize peroxynitric acid. The use of nitrite and acid leads to synthesis of peroxynitric acid at a low cost.

Examples of the nitrite include sodium nitrite ($NaNO_2$), potassium nitrite ($KNO_2$), calcium nitrite ($Ca(NO_2)_2$), and nitronium tetrafluoroborate ($NO_2BF_4$). Any type of cations may be used as long as the nitrite is used.

As the method for synthesizing nitrous acid ($HNO_2$), a method can be used in which nitrogen dioxide gas ($NO_2$) is dissolved into aqueous solution. Alternatively, peroxynitric acid ($HOONO_2$) can be synthesized by dissolving nitrogen dioxide gas ($NO_2$) into aqueous solution having peroxide mixed in advance. Yet alternatively, peroxynitric acid ($HOONO_2$) can be synthesized by using non-ionic solid such as nitrogen pentoxide ($N_2O_5$) or nitrate ($N_2O_6$). As described above, for synthesis of peroxynitric acid ($HOONO_2$), it is possible to use a substance which is dissolved into water to produce nitrous acid or nitrous acid ions.

Instead of synthesizing peroxynitrite from nitrous acid and peroxide to use the peroxynitrite as a material for synthesis of peroxynitric acid, commercially available peroxynitrite may be used. The peroxynitrite is stable in a frozen and basic state. The peroxynitrite is sold in a frozen state; however it is expensive. It is thus preferable to synthesize peroxynitrite by using nitrite and hydrogen peroxide.

The peroxide is, for example, sodium percarbonate ($Na_2CO_3 \cdot 1.5H_2O_2$) in addition to the hydrogen peroxide ($H_2O_2$). The percarbonate (sodium percarbonate) is a powdery substance produced by mixing sodium carbonate ($Na_2CO_3$) with hydrogen peroxide ($H_2O_2$) at a molar ratio of 2:3. Water is added to percarbonate, so that hydrogen peroxide is produced. Stated differently, the percarbonate is the source of the hydrogen peroxide. Even when peroxynitric acid is used, the peroxide in synthesis reaction of the peroxynitric acid is hydrogen peroxide. Since being powdery, the percarbonate is convenient for synthesis of peroxynitric acid and for sterilization using the synthesized peroxynitric acid. For example, powdery percarbonate is prepared in a syringe, and water is added to the percarbonate for use. This easily produces hydrogen peroxide for use.

In addition to the percarbonate, examples of the powdery substance which is hydrolyzed to produce hydrogen peroxide include peroxide such as sodium peroxide ($Na_2O_2$), potassium peroxide ($K_2O_2$), and calcium peroxide ($CaO_2$).

In order to produce peroxynitric acid by a reaction of peroxide and nitrite, it is a prerequisite that the pH value is 2 or lower of strong acid. The lower the pH value is, the higher the synthetic efficiency of peroxynitric acid is. To be specific, in order to synthesize peroxynitric acid, it is essentially necessary to satisfy the inequality pH<2 in acidic conditions. It is preferable to satisfy the equality pH=1, pH=0.5, or pH=0. When the pH value drops to zero, the synthetic efficiency is not further improved and becomes approximately constant.

For such acidic conditions, acid, e.g., nitric acid, hydrochloric acid, or sulfuric acid may be used. Necessary amount of such acid is preferably mixed together to adjust solution to have a pH value of 2 or lower.

As for the order in which peroxide, nitrite, and acid are mixed, it is necessary not to mix first nitrite with acid. In view of this, peroxide and nitrite are mixed first, or, peroxide and acid are mixed first and then the resultant is mixed with the remaining substance. Alternatively, all of peroxide, nitrite, and acid are mixed at the same time.

In order to synthesize peroxynitric acid industrially, it is preferable to approximate the pH value to zero to increase the synthetic efficiency. The lower the pH value is, the more the peroxynitric acid is stable. When the pH value is increased, the peroxynitric acid is decomposed quickly. When the pH value reaches 0.5 or lower, a problem of metal corrosion sometimes arises, which is taken into consideration as needed.

In order to use peroxynitric acid for sterilization, it is necessary to adjust the pH value to become 4.8 or lower. The lower the pH value is, the higher the sterilization effect is. However, even if the pH value is lowered to approximately 3 or lower, the sterilization effect is not so changed that much. It is thus practical to adjust the pH value to become a value of approximately 3 to 3.5 for sterilization use.

Therefore, for synthesis of peroxynitric acid, it is preferable to adjust the pH value to become 2 or lower, for example, to fall within the range of 0.5 to 1, to hold the peroxynitric acid in that state, to use buffer solution to dilute the synthesized peroxynitric acid for sterilization, and to adjust the pH value to become 3 to 3.5. The synthesized peroxynitric acid having a pH value of 2 or lower may be used as-is for sterilization without being diluted if no problem arises in the material of an object to be sterilized.

The description goes on to an embodiment of producing peroxynitric acid.

First Embodiment of Producing Peroxynitric Acid

Figure 2:
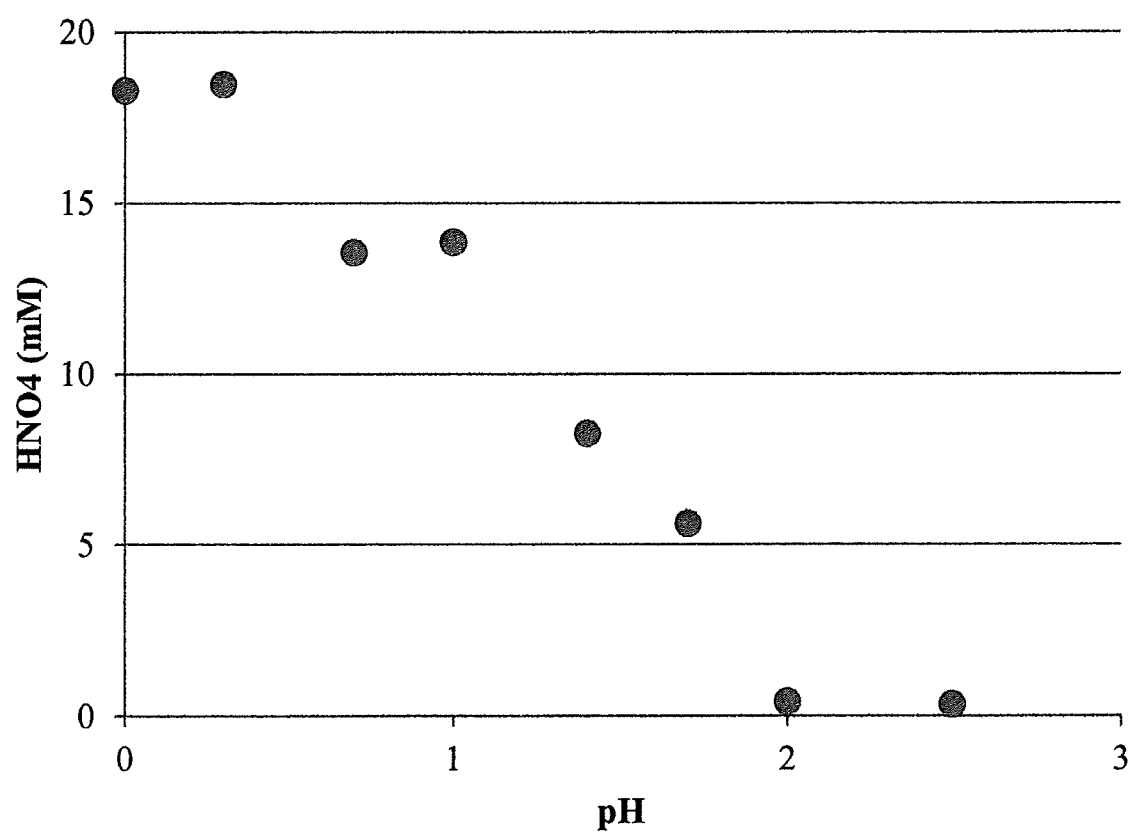
FIG. 2 is a diagram showing a relationship between the concentration of peroxynitric acid produced in the first embodiment and a pH value.

A 50 µL of nitric acid with various concentrations was mixed with a 40 µL of hydrogen peroxide with a concentration (molar concentration) of 1M at an ice cold temperature. A 10 µL of sodium nitrite with a concentration of 1M was mixed with the resultant. FIGS. 1 and 2 show the concentration of peroxynitric acid thus produced. It is noted that, in the Specification, the "concentration" means "molar concentration" except as otherwise noted. The unit of concentration is [M] (Molar), namely, [mol/L].

To be specific, FIG. 1 shows a relationship between the concentration of peroxynitric acid produced in the first embodiment and the concentration of nitric acid, and FIG. 2 shows a relationship between the concentration of peroxynitric acid produced in the first embodiment and a pH value.

Referring to FIG. 1, as the concentration of nitric acid increases, the production of peroxynitric acid increases. After the concentration of nitric acid exceeds 0.5M, the concentration of peroxynitric acid reaches 19 mM and the concentration thereof is approximately constant.

Referring to FIG. 2, little peroxynitric acid is produced at a pH value of 2 or more. At a point of pH value of 2 or lower, the production of peroxynitric acid increases as the pH value is reduced. After the pH value drops to zero, the concentration of peroxynitric acid reaches 19 mM and the concentration thereof is approximately constant.

The foregoing shows that: it is essentially necessary to synthesize peroxynitric acid in a strongly acidic environment with the pH value set at 2 or lower; the pH value is preferably set at 1 or lower in light of the synthetic efficiency; and the synthetic efficiency is approximately constant when the pH value drops to zero.

Second Embodiment of Producing Peroxynitric Acid

Figure 3:
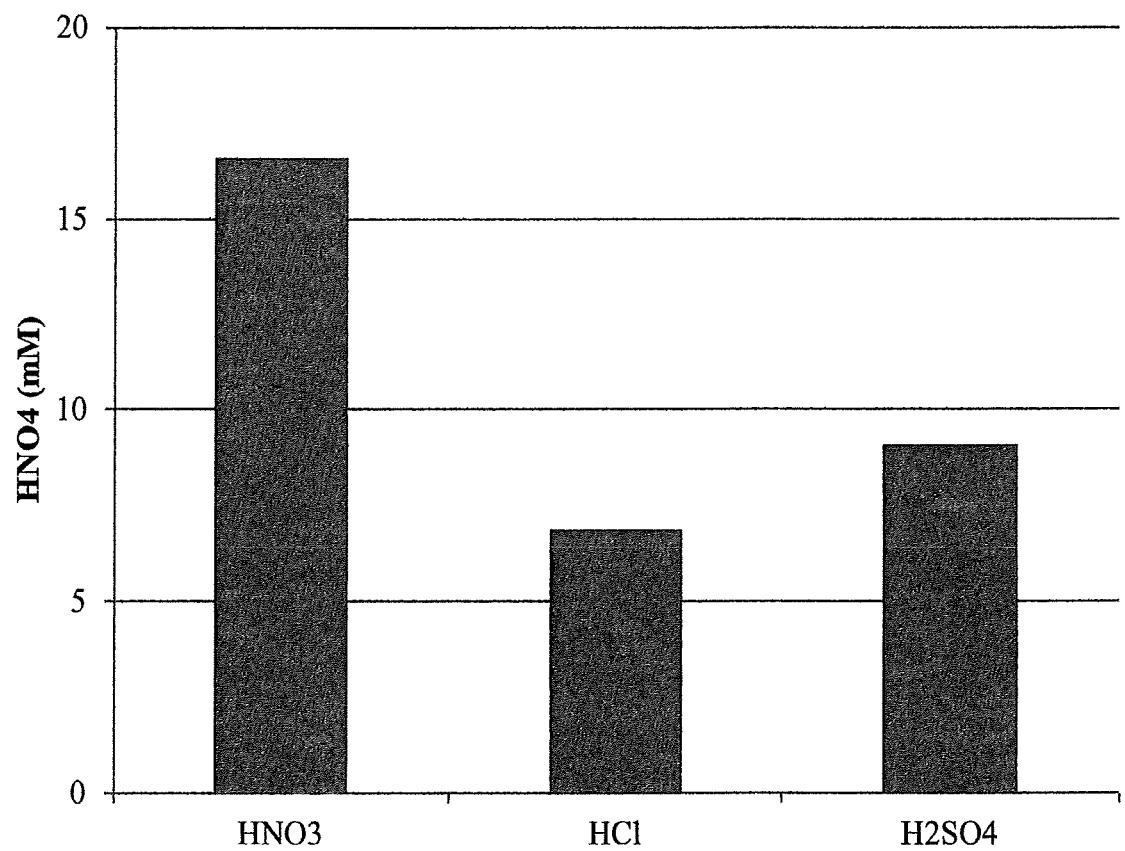
FIG. 3 is a diagram showing a relationship between the concentration of peroxynitric acid produced in a second embodiment and various kinds of acid.

A 40 mL of hydrogen peroxide with a concentration of 1M was mixed with a 10 mL of sodium nitrite with a concentration of 1M at a room temperature. A 50 mL of various types of acid with a concentration of 1N (prescribed) was mixed with the resultant. FIG. 3 shows the concentration of peroxynitric acid thus produced. The acid used herein was nitric acid, hydrochloric acid, or sulfuric acid.

To be specific, FIG. 3 shows a relationship between the concentration of peroxynitric acid produced in the second embodiment and various kinds of acid.

Referring to FIG. 3, when nitric acid, hydrochloric acid, or sulfuric acid was used as the acid, the concentration of the peroxynitric acid was approximately 17 mM, 7 mM, or 9 mM, respectively. This shows that the peroxynitric acid can be synthesized by using any types of the acid, and that the use of nitric acid indicates highest synthetic efficiency.

The nitrous acid eventually turns into nitric acid, and an alkaline substance is also produced. It is not thus expected that the pH value of solution is lowered. The nitrous acid turns into nitric acid, which is the same as the case of using nitric acid as the acid. This however does not provide any particular advantages. The use of nitric acid as the acid increases the concentration of nitrogen compound in a waste fluid. If this possibly causes a problem, hydrochloric acid or sulfuric acid is preferably used as the acid.

Third Embodiment of Producing Peroxynitric Acid

Figure 4:
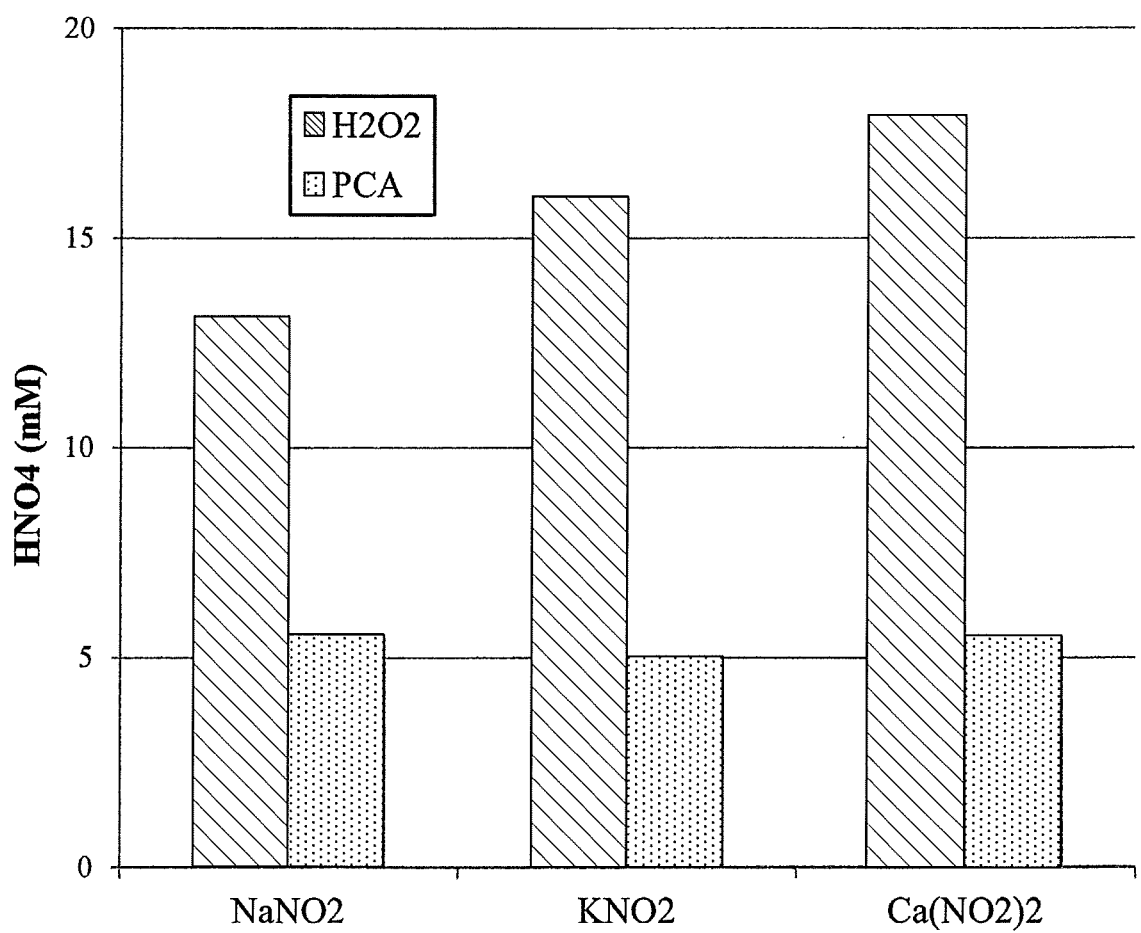
FIG. 4 is a diagram showing a relationship between the concentration of peroxynitric acid produced in a third embodiment and various kinds of peroxide.

An 80 mL of different type of peroxide with a concentration of 1M was mixed with a 20 mL of nitrite with a concentration of 1M at a room temperature. A 100 mL of nitric acid with a concentration of 1N was mixed with the resultant. FIG. 4 shows the concentration of peroxynitric acid thus produced. The peroxide used herein was hydrogen peroxide or percarbonate. The nitrite used herein was sodium nitrite, potassium nitrite, or calcium nitrite.

To be specific, FIG. 4 shows a relationship between the concentration of peroxynitric acid produced in the third embodiment and various kinds of peroxide. In FIG. 4, with each nitrite referred to, a bar graph on the left shows for the case of using hydrogen peroxide and a bar graph on the right shows for the case of using percarbonate (PCA).

Referring to FIG. 4, when the peroxide was hydrogen peroxide and the nitrite was sodium nitrite, potassium nitrite, or calcium nitrite, the concentration of the peroxynitric acid was approximately 13 mM, 16 mM, or 18 mM, respectively. Alternatively, when the peroxide was percarbonate and the nitrite was sodium nitrite, potassium nitrite, or calcium nitrite, the concentration of the peroxynitric acid was approximately 5 mM in all the cases.

The foregoing shows that: the peroxynitric acid can be produced by using any types of nitrite; no significant difference is observed in synthetic efficiency depending on types of nitrite; and synthetic efficiency is higher with hydrogen peroxide than with percarbonate.

Summary of First to Third Embodiments for Producing Peroxynitric Acid

The results of the first through third embodiments show the following.
(1) It is essential to synthesize peroxynitric acid at a pH value of 2 or lower. In view of the synthetic efficiency, peroxynitric acid is preferably synthesized in strongly acidic conditions where the pH value is zero or so.
(2) It is preferable to use nitric acid as acid.
(3) Various types of nitrite can be used, and any kinds of cation can be used.
(4) It is preferable to use hydrogen peroxide as peroxide.

The synthesis reaction of peroxynitric acid progresses also at a room temperature. To be specific, peroxynitric acid is synthesized at a room temperature; however, the lifetime of the synthesized peroxynitric acid depends on temperature. Where being saved at a room temperature, the synthesized peroxynitric acid is quickly decomposed to turn into nitric acid in a short time. When the temperature rises by 5 degrees, the rate of decomposition doubles. For example, the rate of decomposition at a temperature of 20° C. is 16 times as fast as that at a temperature of 0° C. (zero). Thus, the synthesized peroxynitric acid turns into nitric acid solution very quickly at a temperature of 50° C. The half-life of the peroxynitric acid is 10 minutes or so at a room temperature. The half-life of the peroxynitric acid is a few hours (2 to 3 hours or so) at a temperature of 0 (zero) degrees.

At the synthesis of peroxynitric acid, mixing peroxide and nitrite together produces heat. It is therefore preferable to mix them slowly or mix them while cooling them. For example, a vessel or a solution is so cooled that the temperature of peroxynitric acid at the time of synthesis is 10° C. or lower. Alternatively, it is preferable to mix peroxide with nitrite in a vessel having a sufficient heat release effect in a room controlled to have a temperature of 10° C. or lower. In the case of synthesis of peroxynitric acid in a laboratory, peroxide is preferably mixed with nitrite on ice.

Fourth Embodiment under Optimum Conditions for Producing Peroxynitric Acid

In the fourth embodiment, peroxynitric acid was synthesized under conditions considered to be close to the optimum conditions, taking the results of the first through third embodiments into account.

In the fourth embodiment, a 120 mL of hydrogen peroxide with a mass percent concentration of 30%, an 80 mL of nitric acid with 1N, and a 80 mL of sodium nitrite with a mass percent concentration of 60% (8.7 M) were mixed together.

The peroxynitric acid thus synthesized had a concentration of 420 mM, and the synthetic efficiency was 17%. The peroxynitric acid having a high concentration was obtained at a high synthetic efficiency.

In the fourth embodiment, powdery sodium nitrite was dissolved into water, and the resultant was used as the sodium nitrite with a mass percent concentration of 60% (8.7 M). The volume ratio of hydrogen peroxide, nitric acid, and sodium nitrite was set at 3:2:2. Even if each volume (mL) is changed from the foregoing value to another value, the same result can be obtained as long as the volume ratio is kept.

For synthesis of peroxynitric acid, sodium nitrite and hydrogen peroxide react with each other at a molar ratio 1:2. If sodium nitrite is so prepared to exceed the molar ratio 1:2, sodium nitrite is redundant, which is not preferable in light of the synthetic efficiency. In actual, however, no big problem arises until the molar ratio reaches 1:1. In terms of the synthetic efficiency, more hydrogen peroxide is better.

As for nitric acid, the resultant of mixing all preferably has a pH value of 2 or lower. For example, if the concentration of nitric acid is increased, nitric acid having 3N may be used to reduce the amount thereof to one-third. When nitric acid having a large concentration is used, the volume is small and the concentration of peroxynitric acid to be synthesized is further increased.

As discussed above, since the peroxynitric acid has a short lifetime at a high temperature, the peroxynitric acid is cooled to set the temperature at 10° C. for the case where the peroxynitric acid is synthesized.

Sterilization Action by Peroxynitric Acid

The description goes on to a sterilization action and a sterilization effect by peroxynitric acid.

Peroxynitric acid synthesized by chemical reaction probably generates superoxide anion radicals ($O_2$—.) having a very short lifetime as shown in Formula (6) below.

$$HOONO_2 \leftrightarrow H_+ + O_2{-}. + NO_2. \qquad (6)$$

To be specific, peroxynitric acid produces protons ($H_+$), superoxide anion radicals ($O_2$—.), nitrogen dioxide ($NO_2$.), and so on, which are probably diffused into liquid.

In such a case, the superoxide anion radicals ($O_2$—.) have microbicidal activity. The superoxide anion radicals ($O_2$—.), however, have a lifetime in the order of seconds which is extremely shorter than that of peroxynitric acid. As soon as the superoxide anion radicals ($O_2$—.) are produced, the superoxide anion radicals ($O_2$—.) are disappeared instantly. As shown in Formula (7) below, the superoxide anion radicals ($O_2$—.) react with protons ($H_+$) in solution to produce hydroperoxy radicals (HOO.).

$$O_2{-}. + H_+ \leftrightarrow HOO. \qquad (7)$$

The hydroperoxy radicals (HOO.) produced by the reaction shown in Formula (7) have an extremely short lifetime. The hydroperoxy radicals (HOO.) have more powerful microbicidal activity than the superoxide anion radicals ($O_2$—.) have. Formula (7) expresses an equilibrium reaction, and an equilibrium relationship is established depending on a pH value of the solution. Where the protons ($H_+$) have a high concentration, the hydroperoxy radicals (HOO.) have a high concentration.

To be specific, a dissociation constant representing an equilibrium constant of this equilibrium reaction formula (acid dissociation constant), i.e., pKa, is "4.8". Where the pH value is 4.8 or higher, the superoxide anion radicals ($O_2$—.) have a high concentration, and the hydroperoxy radicals (HOO.) have a low concentration. However, where the pH value is adjusted to become 4.8 or lower, the concentration of the hydroperoxy radicals (HOO.) is increased and the hydroperoxy radicals (HOO.) exert extremely powerful microbicidal activity. Stated differently, in order to increase the concentration of the hydroperoxy radicals (HOO.) exerting extremely powerful microbicidal activity, it is necessary to adjust the pH value of the solution to become 4.8 or lower.

Thus, the pH value of the solution containing the produced peroxynitric acid is adjusted to become 4.8 or lower. This increases the concentration of the hydroperoxy radicals (HOO.), so that extremely powerful microbicidal activity is exerted.

As discussed above, it is possible to maintain the concentration of the hydroperoxy radicals (HOO.) at a high level by adjusting the pH value of the solution containing the peroxynitric acid to become 4.8 or lower, so that the solution can obtain a sterilization effect which is equivalent to or greater than that of the plasma-treated solution. In practical, according to the method for producing peroxynitric acid by the chemical reaction, the hydroperoxy radicals (HOO.) having a concentration which is one hundred times higher than that of the plasma-treated solution can be obtained, so that extremely powerful microbicidal activity is exerted.

The peroxynitric acid in the solution is probably a precursor which produces the superoxide anion radicals ($O_2$—.). The superoxide anion radicals ($O_2$—.) are probably precursors which produce the hydroperoxy radicals (HOO.). It was confirmed that, when enzyme for disappearing the superoxide anion radicals ($O_2$—.) is put into the solution, the sterilization effect is not observed.

Figure 14:
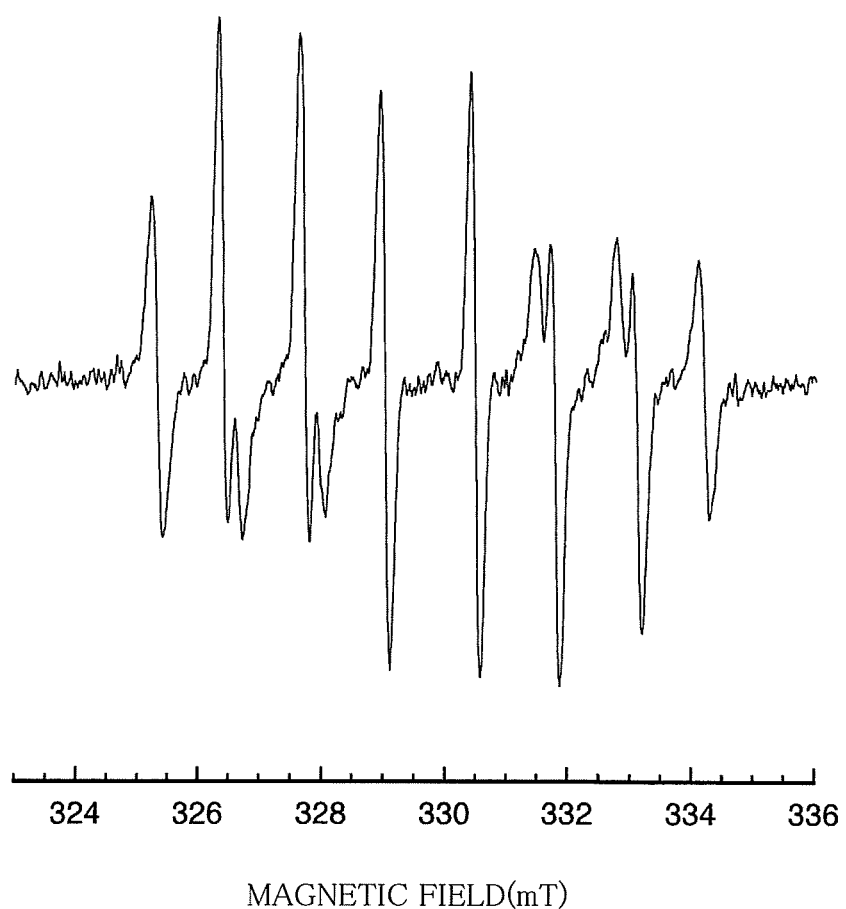
FIG. 14 is a diagram showing electron spin resonance spectrum of a solution containing peroxynitric acid.

An electron-spin resonance method was used to confirm that the solution contains the superoxide anion radicals ($O_2$—.). A spin trapping agent (CYPMPO) was mixed into the solution and an electron-spin resonance device was used to make a measurement. As shown in FIG. 14, a spectrum of spin adduct which reacted with the superoxide anion radicals ($O_2$—.) through the spin trapping agent was generated.

Next, verification is performed that sterilization action is attributable to the peroxynitric acid produced by chemical reaction.

First Verification that Sterilization Action is Attributable to Peroxynitric Acid The solution mixed and synthesized in the fourth embodiment was used as a sample to separate/purify substances by ion chromatography, and a sterilization effect was examined every retention time RT for the substances separated/purified.

Figure 5:
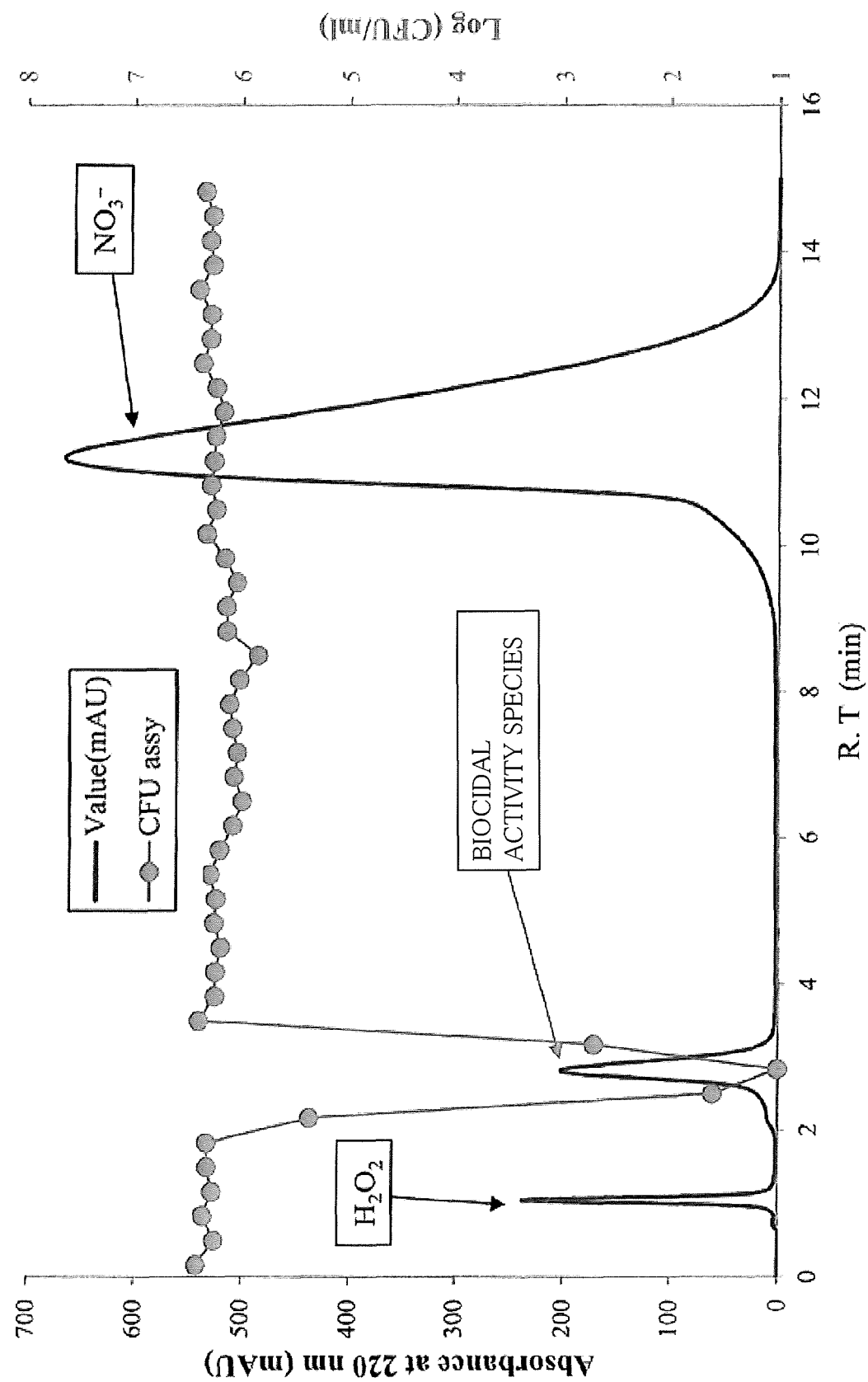
FIG. 5 is a diagram showing a chromatogram of solution produced in a fourth embodiment and a sterilization effect of substances corresponding to different retention times.
Figure 7:
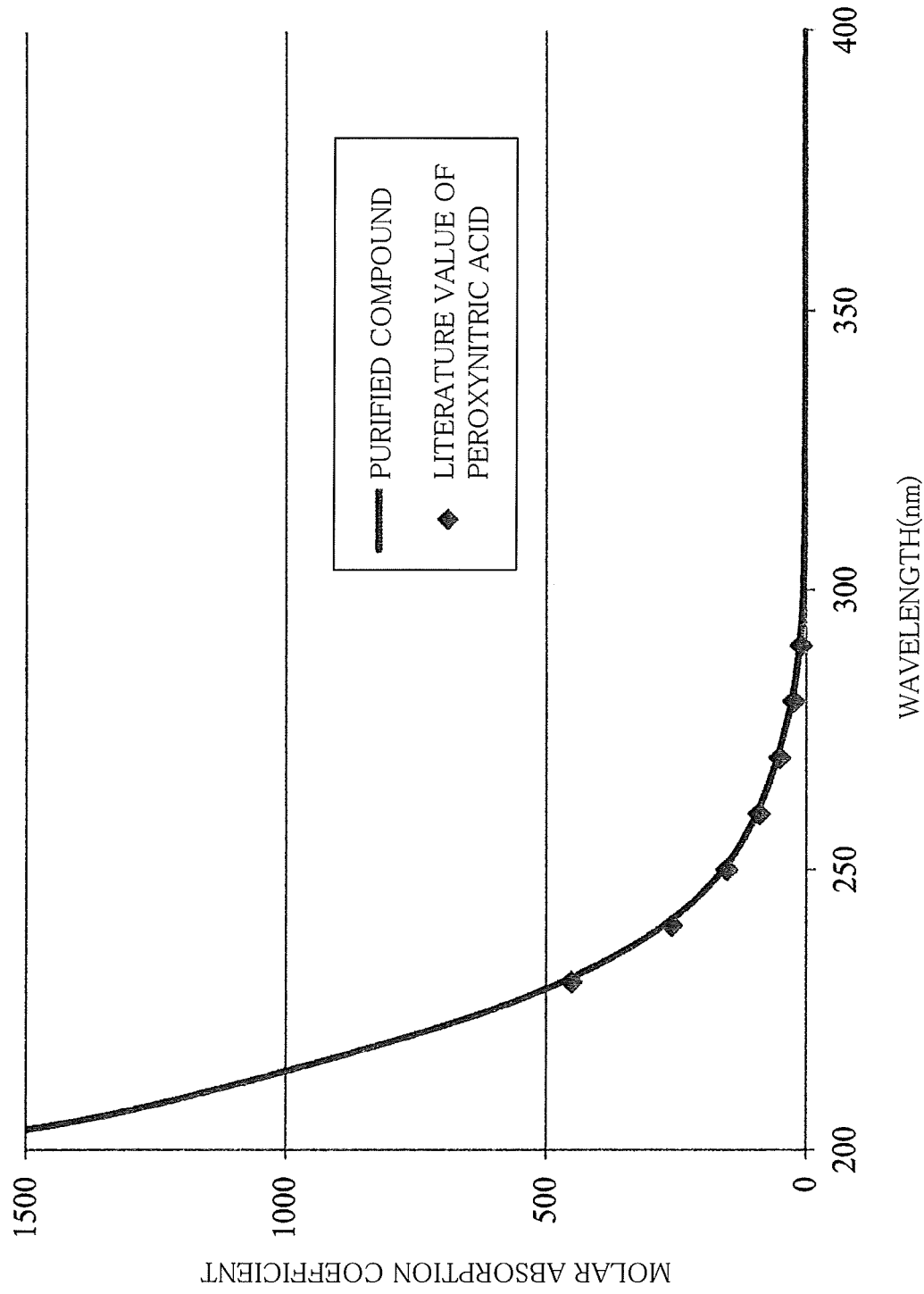
FIG. 7 is a diagram showing a molar absorption coefficient for a substance at a retention time RT of 2.8 minutes in the fourth embodiment.

FIG. 5 shows a chromatogram of the solution mixed and synthesized in the fourth embodiment and a sterilization effect of substances fractionated at different retention times. FIG. 7 shows a curve representing a molar absorption coefficient of ultraviolet rays for a certain substance at a retention time RT of 2.8 minutes in the solution and plotted molar absorption coefficients of ultraviolet rays for peroxynitric acid.

Figure 6:
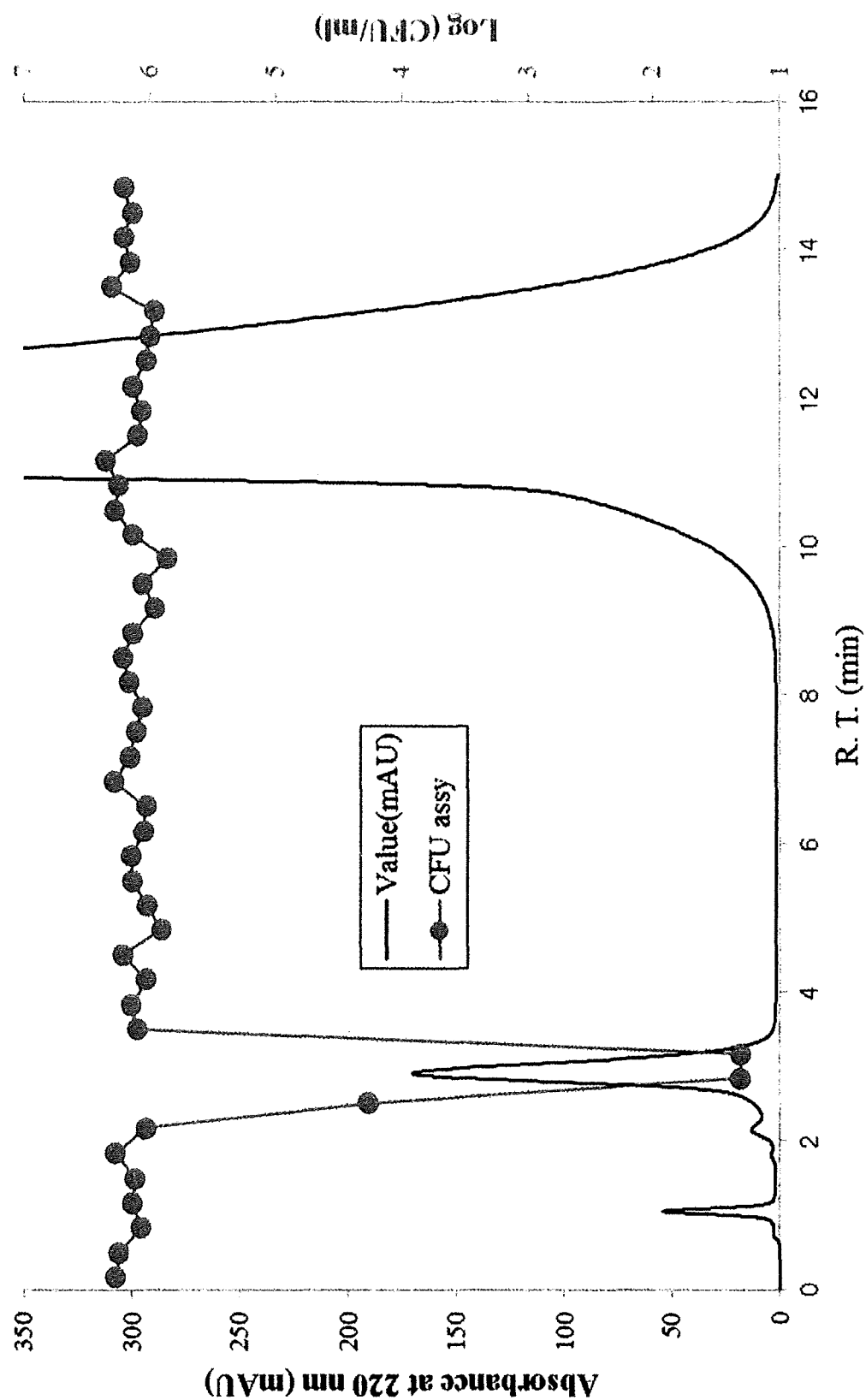
FIG. 6 is a comparison diagram showing a chromatogram of plasma-treated solution and a sterilization effect of substances corresponding to different retention times.

For comparison, FIG. 6 shows a chromatogram of plasma-treated solution and a sterilization effect of substances fractionated at different retention times.

As a separation column, PCI-201S (inner diameter: 4.6 mm; full length: 100 mm) made by DKK-TOA Corporation was used. The column was disposed in ice to have a temperature of 0° C. to prevent peroxynitric acid (pernitric acid) from being decomposed during the measurement. The mobile phase was prepared to set strong acid such as hydrochloric acid, perchloric acid, and methanesulfonic acid at a predetermined concentration, and the flow rate was fixed at 1.5 ml/min. For detection, a UV detector (measurement wavelength: 220 nm) or a photo diode array detector (measurement wavelength: 200 to 400 nm) was used. Eluant used was solution which contains hydrochloric acid (HCl) having a concentration of 10 mM and has a pH value of 2.0.

Referring to FIG. 5, peaks appear in the chromatogram at retention times RT of 1 minute, 2.8 minutes, and 11.1 minutes. The peak at a retention time RT of 2.8 minutes corresponds to the position of a trough of a plot line for sterilization effect. This shows that a substance corresponding to the retention time RT of 2.8 minutes is biocidal activity species.

In FIG. 5, the vertical axis for sterilization effect shows a LOG value of a colony-forming unit (CFU) which is the number of living microorganisms contained in an evaluation target. The trough for sterilization effect is observed only at a position of a retention time RT of 2.8 minutes.

From FIG. 7, it can be seen that plot positions (literature values) of a molar absorption coefficient of peroxynitric acid sufficiently correspond to a curve representing a molar absorption coefficient of a substance having a retention time RT of 2.8 minutes. Therefore, a substance corresponding to a retention time RT of 2.8 minutes is probably peroxynitric acid.

A substance corresponding to a peak of a retention time RT of 1 minute is hydrogen peroxide. A substance corresponding to a peak of a retention time RT of 11.1 minutes is a nitric acid ion.

It is thus conceivable that the high biocidal activity of the solution mixed and synthesized in the fourth embodiment comes from peroxynitric acid.

The molar absorption coefficient of peroxynitric acid herein is cited from the following document.

Inorg. Chem. 1995, 34, 787-791 "Aqueous Peroxynitric Acid ($HOONO_2$): A Novel Synthesis and Some Chemical and Spectroscopic Properties".

FIG. 6 shows a chromatogram based on the same ion chromatography with plasma-treated solution used as a sample, and sterilization effect of substances corresponding to different retention times RT, which are remarkably similar to those shown in FIG. 5. A peak at a retention time RT of 2.8 minutes corresponds to a trough of a plot line for sterilization effect.

It is thus probable that the biocidal activity species in the solution mixed and synthesized in the fourth embodiment are the same substance as the biocidal activity species in the plasma-treated solution, and that the substance is peroxynitric acid.

Second Verification that Sterilization Action is Attributable to Peroxynitric Acid As for the substance corresponding to the retention time RT of 2.8 minutes shown in FIG. 5, a half-life of the substance was actually measured at a pH value of 4.7 and a temperature of 20° C. The half-life measured was compared to a half-life (literature value) of peroxynitric acid under the same conditions as those above. The comparison result is provided as follows:

Actual measured value: 0.50 minutes

Literature value: 0.51 minutes

Both the values are in good accord with each other. Thereby, the substance corresponding to the retention time RT of 2.8 minutes is probably peroxynitric acid.

The half-life of peroxynitric acid herein was cited from the following document.

J. Am. Chem. SOC. 1981, 103, 2203-2206 "Preparation and Thermal Decomposition of Pernitric Acid ($HOONO_2$) in Aqueous Media"

Third Verification that Sterilization Action is Attributable to Peroxynitric Acid As for the substance corresponding to the retention time RT of 2.8 minutes shown in FIG. 5, an activation energy in decomposition response thereof was actually measured. The activation energy measured was compared to an activation energy in decomposition response of peroxynitric acid. The comparison result is provided as follows:

Actual measured value: 109 kJ/mol

Literature value: 110 kJ/mol

Both the values are in good accord with each other. Thereby, the substance corresponding to the retention time RT of 2.8 minutes is probably peroxynitric acid.

The activation energy in decomposition response herein was cited from the following document.

J. Phys. Chem. A 1997, 101, 8822-8829 "Peroxynitric Acid Decay Mechanisms and Kinetics at Low pH".

The first through third verifications draw the following conclusion: The high biocidal activity in the solution mixed and synthesized in the fourth embodiment comes from peroxynitric acid, and the high sterilization effect is achieved by virtue of liquid containing the peroxynitric acid.

Further, the first through third verifications draw the following conclusion: Biocidal activity species in the solution synthesized by chemical reaction in the fourth embodiment are the same substance as biocidal activity species in the plasma-treated solution generated by physical reaction using plasma, and the substance is peroxynitric acid.

It is also possible to perform mass spectrometry on the substance corresponding to the retention time RT of 2.8 minutes. However, this is not appropriate because the substance is decomposed during the mass spectrometry.

Sterilization Effect of Peroxynitric Acid Produced by Chemical Reaction

The description goes on to the result of experiment conducted on sterilization effect of peroxynitric acid synthesized by chemical reaction.

Figure 8:
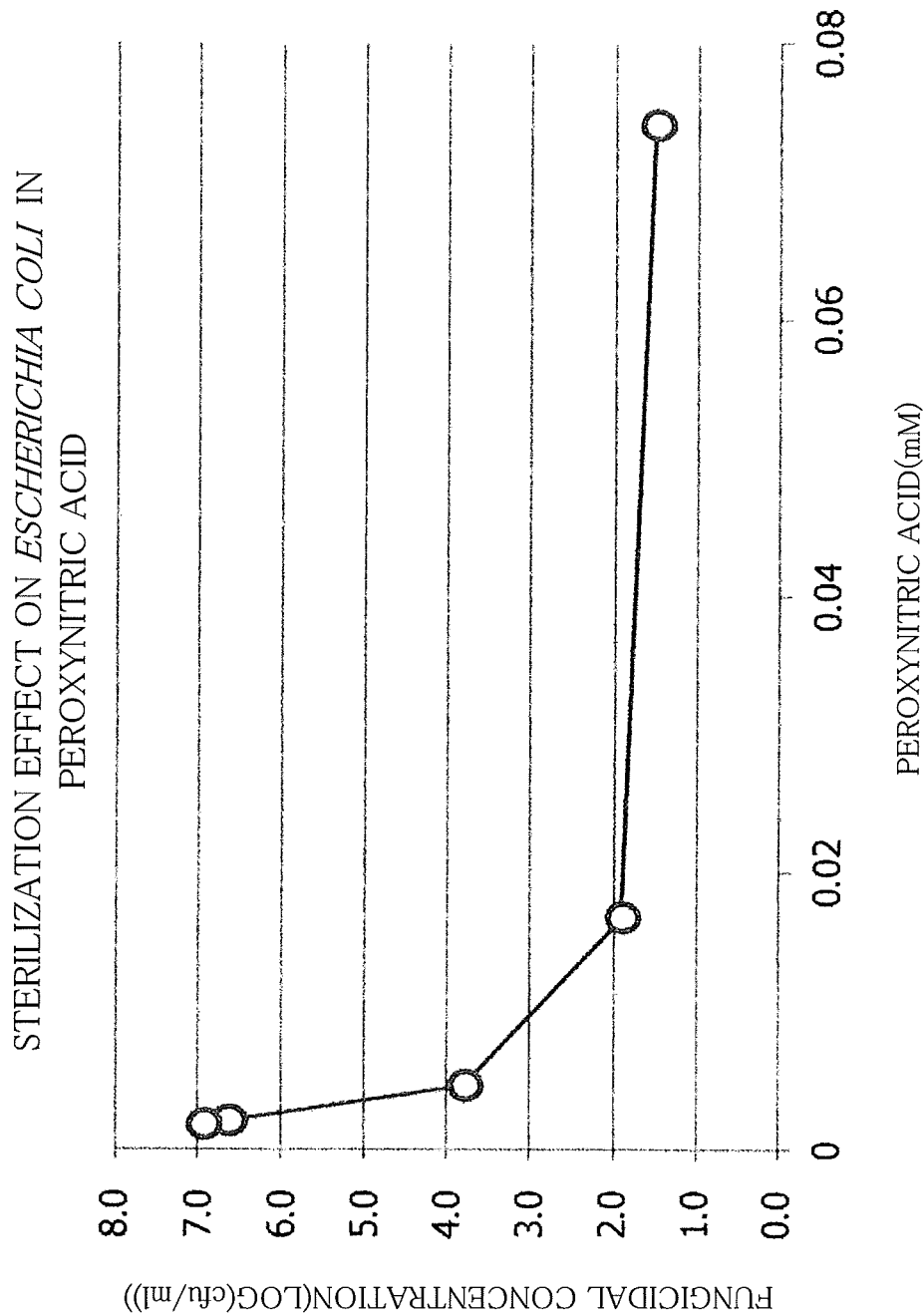
FIG. 8 is a diagram showing a sterilization effect on *Escherichia coli* in the synthesized peroxynitric acid.
Figure 9:
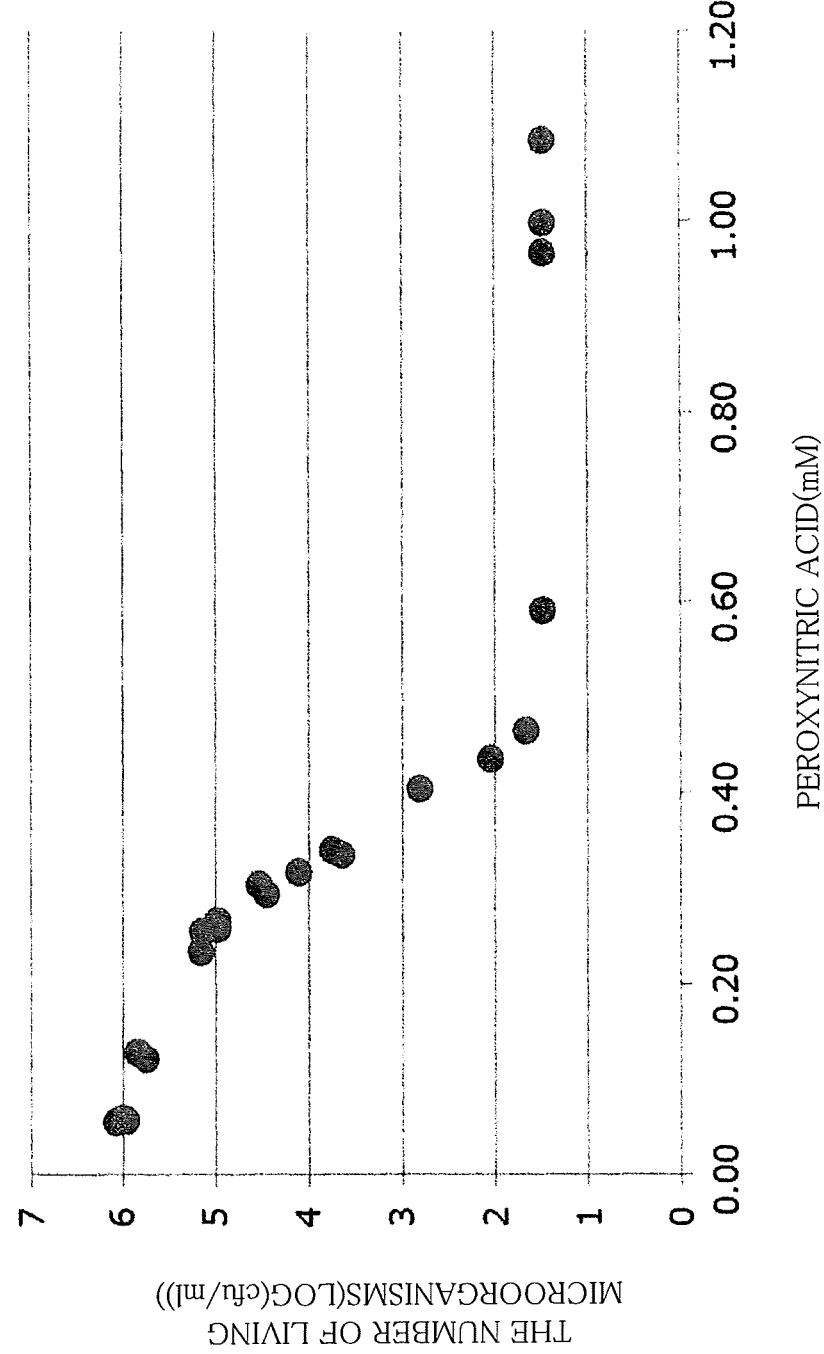
FIG. 9 is a diagram showing a sterilization effect on *Bacillus subtilis* spore in the synthesized peroxynitric acid.
Figure 10:
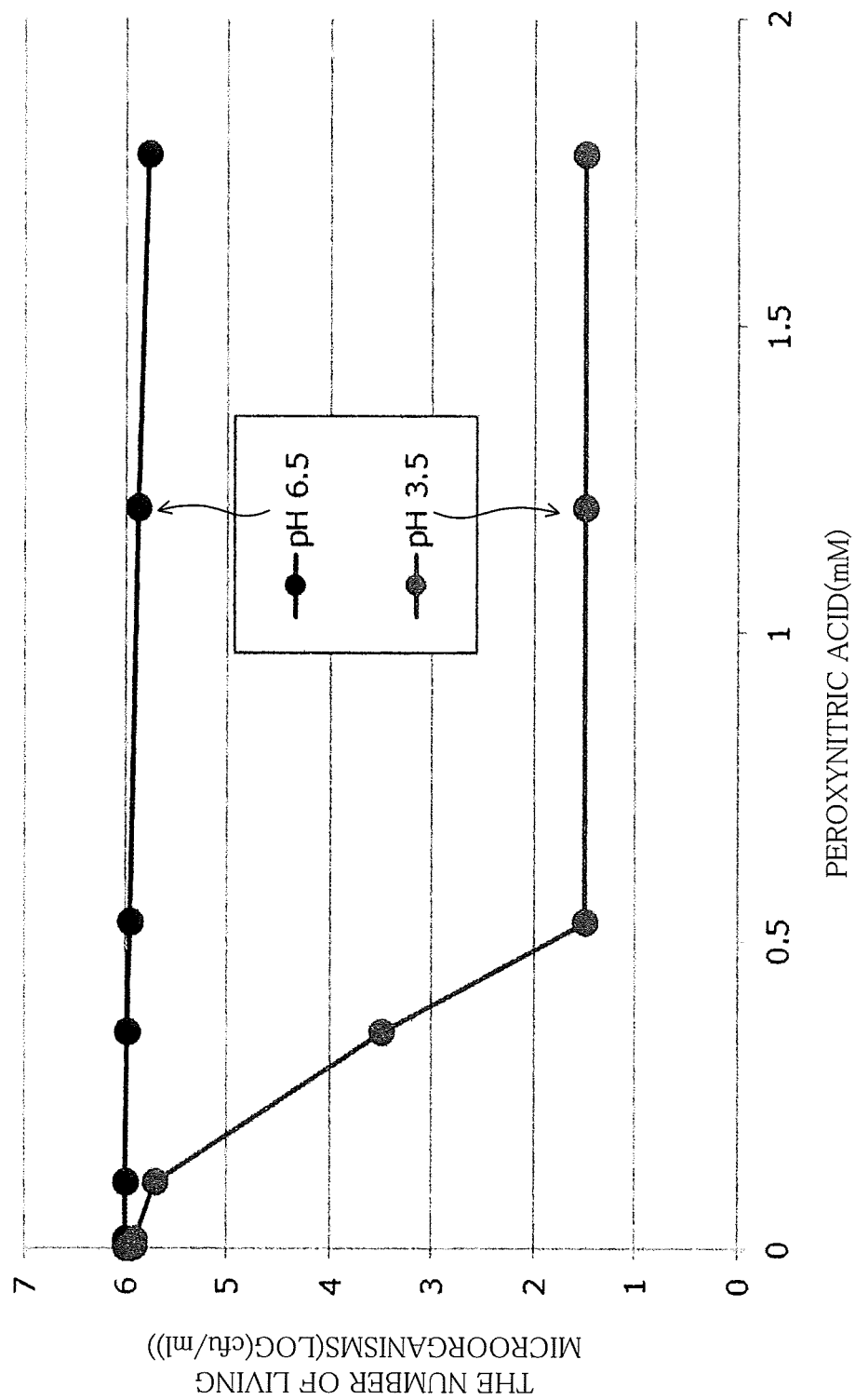
FIG. 10 is a diagram showing an influence of pH value on a sterilization effect on *Bacillus subtilis* spore in the synthesized peroxynitric acid.
Figure 11:
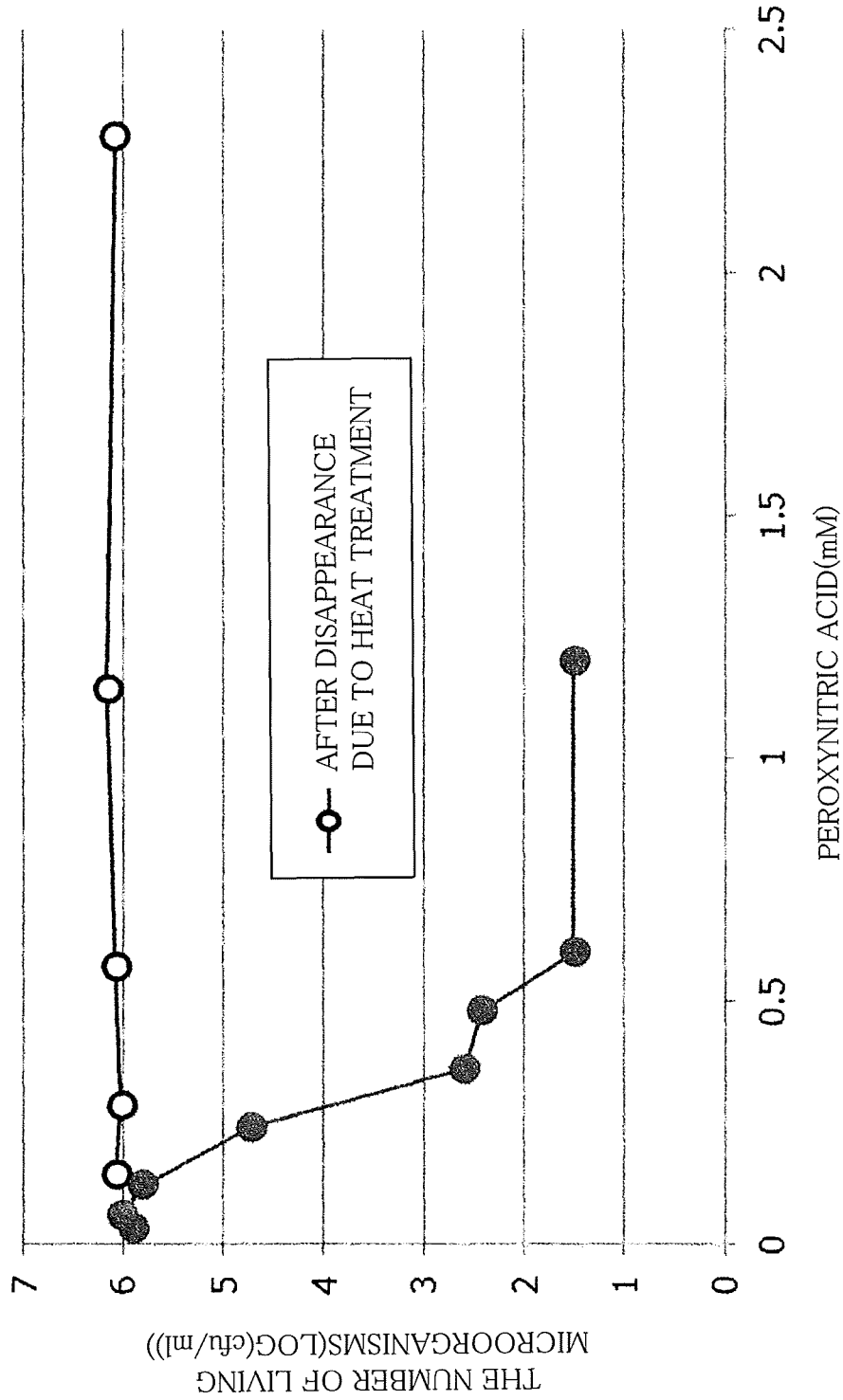
FIG. 11 is a diagram showing disappearance, due to heat treatment, of biocidal activity on *Bacillus subtilis* spore in the synthesized peroxynitric acid.

FIG. 8 shows a sterilization effect on *Escherichia coli* in the synthesized peroxynitric acid. FIG. 9 shows a sterilization effect on *Bacillus subtilis* spore in the synthesized peroxynitric acid. FIG. 10 shows an influence of pH value on a sterilization effect on *Bacillus subtilis* spore in the synthesized peroxynitric acid. FIG. 11 shows disappearance, due to heat treatment, of biocidal activity on *Bacillus subtilis* spore in the synthesized peroxynitric acid.

In FIGS. 8, 9, and 11, solution of peroxynitric acid has a pH value of 3.5 and a temperature of 25° C. In the heat treatment of FIG. 10, the solution of peroxynitric acid is heated for thirty minutes to have a temperature of 60° C.

As shown in FIG. 8, where the synthesized peroxynitric acid has a concentration of approximately 0.02 mM or higher, the fungicidal concentration of *Escherichia coli* drops from 7 orders of magnitude to 2 orders of magnitude or less, which indicates a drop of 5 orders or more.

As shown in FIG. 9, where the synthesized peroxynitric acid has a concentration of approximately 0.5 mM or higher, the number of living microorganisms in *Bacillus subtilis* spore drops from 6 orders to 2 orders or less, which indicates a drop of 4 orders or more.

As shown in FIG. 10, where the solution of the synthesized peroxynitric acid has a pH value of 6.5, the number of living microorganisms in *Bacillus subtilis* spore is in 6 orders of magnitude and approximately constant independently of the concentration of the peroxynitric acid. Where the solution of the synthesized peroxynitric acid has a pH value of 3.5 and the peroxynitric acid has a concentration of approximately 0.5 mM or higher, the number of living microorganisms in *Bacillus subtilis* spore drops from 6 orders of magnitude to 2 orders of magnitude or less, which indicates a drop of 4 orders of magnitude or more.

As shown in FIG. 11, where the synthesized peroxynitric acid is subjected to heat treatment, the number of living microorganisms in *Bacillus subtilis* spore is in 6 orders of magnitude and approximately constant independently of the concentration of peroxynitric acid, which indicates disappearance of sterilization effect.

In this experiment, the detection limit was reached when the number of living microorganisms was in 2 orders of magnitude or less, then further sterilization effect was not measured. Thus, if the concentration of the synthesized peroxynitric acid is further increased, the number of living microorganisms is expected to be further reduced. In the experiment, diluted solution of the synthesized peroxynitric acid was used. If undiluted solution is used, more powerful microbicidal activity is expected to be exerted. The peroxynitric acid synthesized in the fourth embodiment has a concentration of 420 mM. For example, using undiluted solution of the synthesized peroxynitric acid probably lowers the number of living microorganisms to further 3000 orders of magnitude or more.

Sterilization Method Using Peroxynitric Acid Produced by Chemical Reaction

The description goes on to sterilization methods using peroxynitric acid synthesized by chemical reaction.

One of such methods is to directly apply solution containing peroxynitric acid synthesized by chemical reaction as-is to an object to be sterilized. To be specific, when the object to be sterilized is a living body, water, or small object, for example, the solution is dropped from a dropper, spray, syringe, or small vessel onto the object to be sterilized, or is applied to the object to be sterilized. Alternatively, when the object to be sterilized is medical equipment, food container, or other article, the solution is held in an appropriate container and the object to be sterilized is put into the container to be soaked into the solution.

It is noted, however, that since the solution has a pH value of 2 or lower, in order to apply the solution to an object which is not resistant to a low pH value, it is necessary to dilute the solution by using buffer solution to have an appropriate pH value of 4.8 or lower, for example, a pH value of 3 to 3.5. Peroxynitric acid having a lower pH value has a longer lifetime. It is thus preferable to dilute peroxynitric acid with the buffer solution immediately before sterilization.

The buffer solution is, for example, citric acid, acidum tartaricum, phthalic acid, or glycine.

Where the solution has a temperature of 10° C. or lower, the solution may be applied to an object to be sterilized with the temperature remaining unchanged. It is also possible to raise the temperature of the solution to 20° C. or more at the time of application of the solution to the object to be sterilized. It is preferable for the solution to have a lower temperature in order to preserve peroxynitric acid, but at the same time, is preferable for the solution to have a certain level of high temperature for sterilization. To be specific, while the solution having a temperature of 0° C. needs time to sterilize the object, the solution having a temperature of 30° C. needs only 20 seconds to sufficiently sterilize the object. When the situation permits to take time to sterilize the object, it is preferable to perform sterilization at a low temperature. When quick sterilization is needed, it is preferable to raise the temperature, for example, to 30 through 40° C.

In order to preserve the solution with the biocidal activity maintained, it is preferable to set the temperature of the solution as low as possible. For example, the solution is adjusted to have a temperature of 0° C., which enables the solution to be stored/preserved for a couple of hours, for example, for 5 to 8 hours or so. Freezing the solution allow the solution to be preserved for a longer time.

Suppose that, for example, the solution is used for sterilization for dental treatment. Since an oral temperature is approximately 37° C. which is the body temperature, it is preferable to adjust the solution to have a temperature and pH value corresponding thereto. In such a case, the solution adjusted to have a temperature of, for example, approximately 20° C. does not make a patient uncomfortable because he/she does not feel cold. It is also preferable to adjust the solution to have a temperature of approximately 20° C. for the case where the solution is used to disinfect a wound area by injury, burn, or bedsore and to kill pylori bacteria in stomach.

In order to use the solution for sterilization of household bath, sink, or wall, it is preferable to adjust the solution to have a pH value of approximately 3 to 4. For using the solution to sterilize dishes, it is preferable to adjust the solution to have a pH value of 3 or so and clean the dishes with water. Once peroxynitric acid is introduced in the body, biocidal activity of peroxynitric acid disappears in a short time due to the body temperature; therefore the peroxynitric acid can be eaten without being cleaned.

Other than those mentioned above, various sterilization methods can be used.

As discussed above, the use of solution (liquid) containing peroxynitric acid obtained by chemical reaction makes it possible to achieve microbicidal activity which is equal to or more powerful than the plasma-treated solution without using a plasma generation device.

Production Device of Sterilizing Liquid Containing Peroxynitric Acid

The description goes on to a production device 1 for producing sterilizing liquid containing peroxynitric acid.

Figure 12:
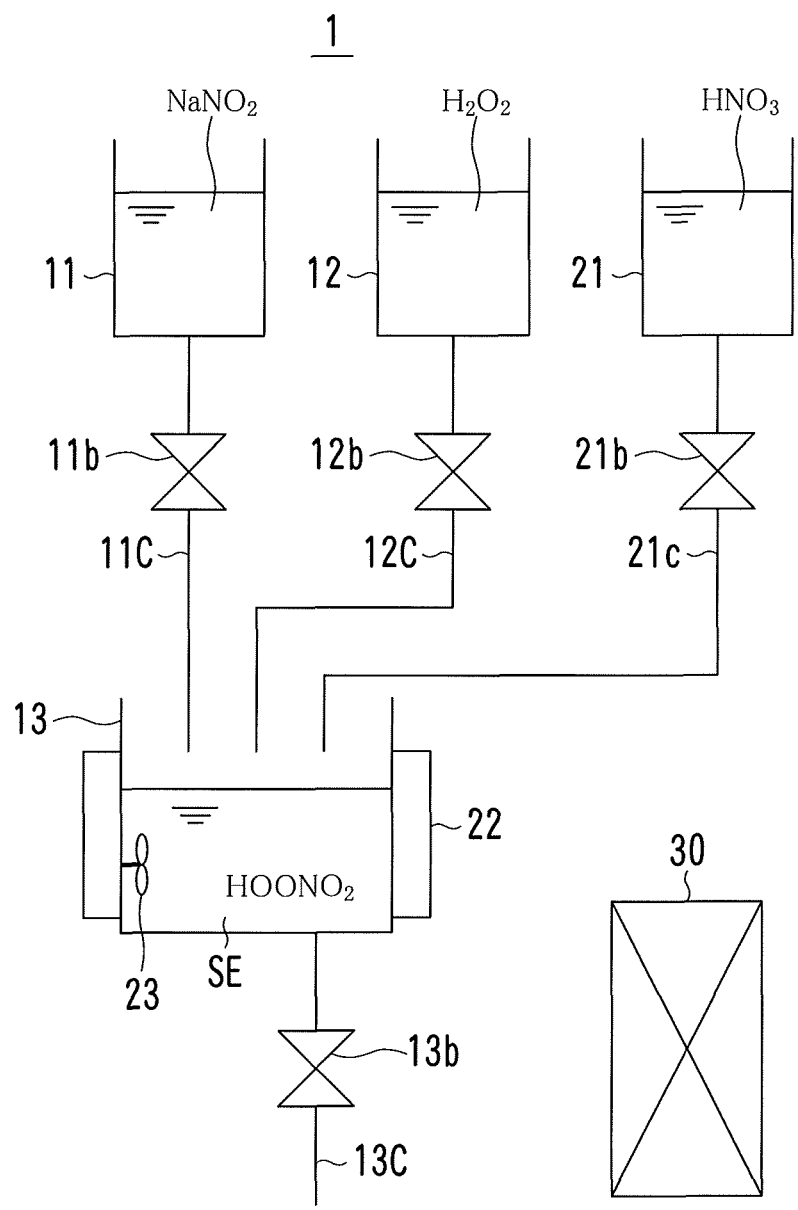
FIG. 12 is a schematic diagram showing an example of the structure of a device for producing sterilizing liquid containing peroxynitric acid.

FIG. 12 shows an example of the outline of the structure of the production device 1 for producing sterilizing liquid containing peroxynitric acid.

Referring to FIG. 12, the production device 1 is configured of a first tank 11, a second tank 12, a third tank 13, an acid supply tank 21, an acid pipe line 21c, a cooling device 22, a stirrer 23, a controller 30, and so on.

The first tank 11 holds nitrite such as sodium nitrite therein. The second tank 12 holds peroxide such as hydrogen peroxide therein. The acid supply tank 21 holds, therein, acid such as nitric acid to be used to adjust a liquid to be mixed in the third tank 13 to become a pH value of 2 or less.

The first tank 11, the second tank 12, and the acid supply tank 21 are coupled through valves 11b, 12b, and 21b to pipe lines 11c, 12c, and 21c, respectively. The pipe lines 11c, 12c, and 21c open into the third tank 13. When the valves 11b, 12b, and 21b are opened, the pipe lines 11c, 12c, and 21c send out the liquid held in each of the tanks to the third tank 13.

In the third tank 13, the nitrite sent out from the first tank 11 and the peroxide sent out from the second tank 12 are mixed together to provide a sterilizing liquid SE containing peroxynitric acid. The third tank 13 is coupled through a valve 13b to a retrieval line 13c from which the sterilizing liquid SE containing peroxynitric acid of the third tank 13 is obtained.

The valves 11b, 12b, 21b, and 13b are electromagnetically operated valves. The controller 30 controls the ON/OFF of the valves 11b, 12b, 21b, and 13b.

The cooling device 22 cools a liquid supplied to the third tank 13 and the mixed sterilizing liquid SE to have a temperature of approximately 10° C. The stirrer 23 stirs the liquid to be mixed in the third tank 13.

The controller 30 controls the ON/OFF of the valves 11b, 12b, 21b, and 13b, the operation of the cooling device 22 and stirrer 23, and so on. The controller 30 controls the order and quantity of each liquid to be sent to the third tank 13. The production device 1 is provided with different sensors (not shown) each of which detects a temperature, level, flow rate, pH value, and so on of each liquid and the sterilizing liquid SE and sends the detected signals to the controller 30.

The production device 1 is provided with a pump for transferring the liquid or the sterilizing liquid SE as necessary. The pump is controlled by the controller 30.

The controller 30 has various buttons with which an operator performs operation. Operating the buttons enable automatic operation and manual operation of the production device 1.

In the automatic operation, each liquid is supplied to the third tank 13 in a predetermined order and mixed together therein, so that a sterilizing liquid SE containing peroxynitric acid is synthesized. The sterilizing liquid SE is cooled at a predetermined temperature and stored in the third tank 13. In response to a button operated, a predetermined quantity of the sterilizing liquid SE is promptly discharged from a retrieval line 13c.

The production device 1 according to this embodiment can be used to easily produce a sterilizing liquid SE in which powerful microbicidal activity is achieved at a low cost. Further, the production device 1 enables the sterilizing liquid SE to be discharged and used whenever necessary.

Instead of supplying the acid contained in the acid supply tank 21 to the third tank 13, or, in addition thereto, the acid in the acid supply tank 21 may be supplied to the second tank 12, and hydrogen peroxide in the second tank 12 may be adjusted to become a pH value of an appropriate value of 2 or lower.

Formulation for Sterilization Use

The description goes on to a formulation for sterilization use 3 which is applied to an object to be sterilized to sterilize the object.

Figure 13:
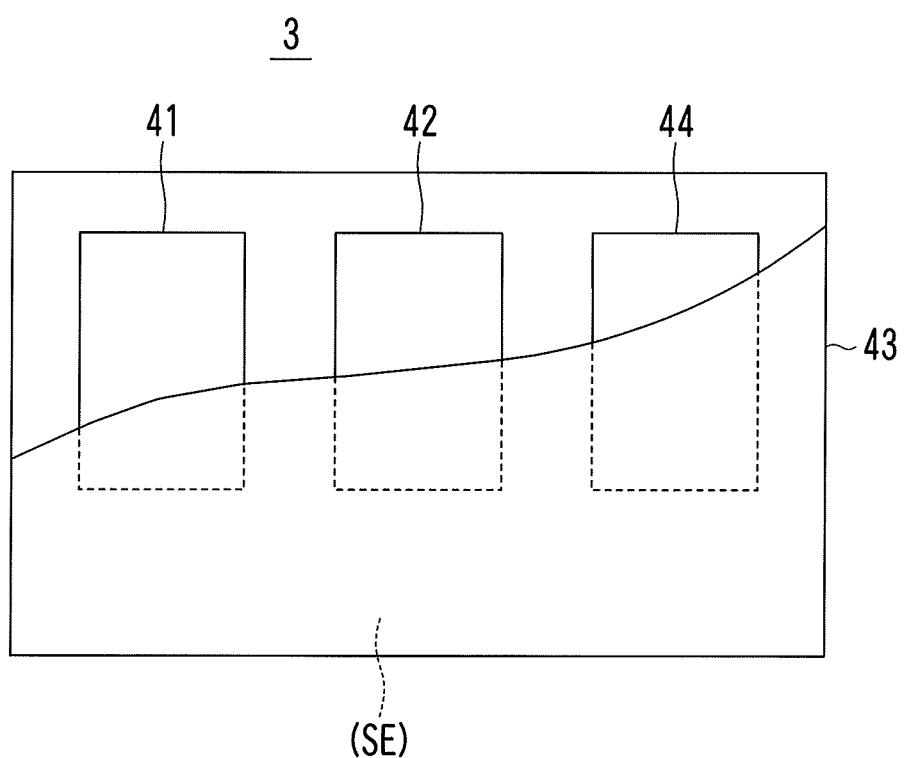
FIG. 13 is a schematic diagram showing an example of the constitution of formulation for sterilization use.

FIG. 13 is a schematic diagram showing an example of the constitution of the formulation for sterilizatio use 3.

Referring to FIG. 13, the formulation for sterilization use 3 is configured of a first case 41, a second case 42, a third case 43, a fourth case 44, and so on. The cases can be, for example, film-like pouches made of paper or synthetic resin.

The first case 41 contains, therein, nitrite or the precursor thereof. The second case 42 contains, therein, peroxide or the precursor thereof. The third case 43 is used to obtain liquid containing peroxynitric acid by mixing the nitrite or the precursor thereof coming out from the first case 41 with the peroxide or the precursor thereof coming out from the second case 42.

The first case 41, the second case 42, and the fourth case 44 are provided inside the third case 43. The first case 41, the second case 42, and the fourth case 44 are torn or opened by, for example, pushing the outer surface of the third case 43 with a finger or the like. As a result, substance or liquid contained therein come out and are mixed together inside the third case 43.

The second case 42 or the third case 43 holds therein acid for adjusting the resultant liquid in the third case 43 to become a pH value of 2 or lower. Instead of this, however, another case may be provided to hold acid therein. The fourth case 44 holds therein a buffer solution to dilute the resultant liquid obtained after the mixture in the third case 43 to become a pH value of 3 to 4.8 for application to an object to be sterilized.

For use in sterilization, the formulation for sterilization use 3 is torn by pushing the first case 41 and the second case 42 with finger or the like, so that the substance or liquid held therein come out to the third case 43. This mixes, in the third case 43, the peroxide or the precursor thereof and the nitrite or the precursor thereof together, and after that, peroxynitric acid is synthesized, so that a liquid containing the peroxynitric acid is obtained. After the liquid containing the peroxynitric acid is obtained, the fourth case 44 is torn so that a buffer solution held therein comes out to adjust the liquid containing the peroxynitric acid to become a pH value of 3 to 4.8. As a result, sterilizing liquid SE is produced. Then, the third case 43 is torn so that the sterilizing liquid SE comes out to sterilize an object to be sterilized.

According to the formulation for sterilization use 3 of this embodiment, the sterilizing liquid SE in which powerful microbicidal activity is achieved can be obtained, when necessary, easily and inexpensively without using any tools. The formulation for sterilization use 3 can be reduced in size and weight, which is convenient to carry around. The formulation for sterilization use 3 may be disposable.

Treatment by Sterilizing Liquid Containing Peroxynitric Acid

The description goes on to a treatment by sterilizing liquid containing peroxynitric acid.

To be specific, the treatment is performed by applying liquid containing peroxynitric acid ($HOONO_2$) obtained by chemical reaction to a living body under acidic conditions of a pH value of 4.8 or lower to sterilize the living body.

For example, the liquid (solution) containing peroxynitric acid is applied as-is to a tooth or gingiva for dental treatment, so that sterilization is performed.

Biocidal activity by peroxynitric acid is safe because the peroxynitric acid enters in the body to disappear in a short time due to the body temperature.

The production device 1 or the formulation for sterilization use 3 can be used as a treatment device using sterilizing liquid.

In the embodiments discussed above, the kind, form, amount of nitrite, peroxide, acid, and so on can be arbitrarily modified in various ways. The temperature and pH value for the case of synthesizing the sterilizing liquid SE, and so on can be arbitrarily modified in various ways.

In the embodiments discussed above, the configurations of all or part of the production device 1 and the formulation for sterilization use 3, structures, shapes, quantities, arrangements, forms, materials thereof, and so on can be arbitrarily modified in various ways within the spirit of the present invention.

What is claimed is:

1. A sterilization method comprising:
   synthesizing peroxynitric acid ($HOONO_2$) by chemical reaction under acidic conditions of a pH value of 2 or lower to preserve a liquid containing the peroxynitric acid ($HOONO_2$); and
   diluting the preserved liquid containing the peroxynitric acid ($HOONO_2$) with a buffer solution, and applying the resultant liquid to an object to be sterilized under acidic conditions of a pH value of 4.8 or lower, thereby to increase the concentration of hydroperoxy radicals (HOO.) produced in the preserved liquid containing the peroxynitric acid ($HOONO_2$); and
   sterilizing the object to be sterilized by microbicidal activity of the hydroperoxy radicals (HOO.).

2. The sterilization method according to claim 1, wherein the preserved liquid containing the peroxynitric acid is produced by mixing a nitrite and peroxide together.

3. The sterilization method according to claim 1, wherein the preserved liquid containing the peroxynitric acid is produced by dissolving nitrous acid gas into an aqueous solution so as to be mixed with a peroxide.

4. The sterilization method according to claim 1, comprising
   synthesizing, by mixing a nitrite, peroxide, and acid together to produce a liquid having a pH value of 2 or lower, to produce the preserved liquid containing the peroxynitric acid,
   using a buffer solution to dilute the preserved liquid containing the peroxynitric acid to produce a liquid having a pH value of 3 to 4.8, and
   applying the liquid having a pH value of 3 to 4.8 to the object to be sterilized.

5. The sterilization method according to claim 4, wherein the acid is mixed with the peroxide to produce a liquid having a pH value of 2 or lower, and
   the liquid having a pH value of 2 or lower is mixed with the nitrite to synthesize the peroxynitric acid.

6. The sterilization method according to claim 4, wherein the liquid is adjusted to have a temperature of 10° C. or lower when the peroxynitric acid is synthesized,
   thereafter, the temperature of the liquid is increased, and the liquid is adjusted to have a temperature of 20° C. or higher when the liquid is applied to the object to be sterilized.

7. The sterilization method according to claim 2, wherein the nitrite is sodium nitrite ($NaNO_2$) and the peroxide is hydrogen peroxide ($H_2O_2$).

8. The sterilization method according to claim 4, wherein the acid is nitric acid ($HNO_3$).

* * * * *